(12) United States Patent
Kono et al.

(10) Patent No.: US 9,193,756 B2
(45) Date of Patent: Nov. 24, 2015

(54) ADRENOMEDULLIN PRODUCTION ENHANCER

(75) Inventors: Toru Kono, Asahikawa (JP); Atsushi Kaneko, Inashiki-gun (JP); Yuji Omiya, Inashiki-gun (JP)

(73) Assignees: National University Corporation ASAHIKAWA MEDICAL COLLEGE, Asahikawa-shi (JP); TSUMURA & Co., Tokyo (JP)

(*) Notice: Subject to any disclaimer, the term of this patent is extended or adjusted under 35 U.S.C. 154(b) by 353 days.

(21) Appl. No.: 12/918,437

(22) PCT Filed: Feb. 19, 2008

(86) PCT No.: PCT/JP2008/052760
§ 371 (c)(1),
(2), (4) Date: Aug. 19, 2010

(87) PCT Pub. No.: WO2009/104248
PCT Pub. Date: Aug. 27, 2009

(65) Prior Publication Data
US 2010/0331270 A1    Dec. 30, 2010

(51) Int. Cl.
*A61K 31/704* (2006.01)
*A61K 31/164* (2006.01)
*C07J 9/00* (2006.01)
*A61K 36/75* (2006.01)
*A61K 36/9068* (2006.01)
*C07J 17/00* (2006.01)

(52) U.S. Cl.
CPC .................. *C07J 9/00* (2013.01); *A61K 31/164* (2013.01); *A61K 31/704* (2013.01); *A61K 36/75* (2013.01); *A61K 36/9068* (2013.01); *C07J 17/005* (2013.01)

(58) Field of Classification Search
CPC ............................ A61K 31/704; A61K 31/164
See application file for complete search history.

(56) References Cited

FOREIGN PATENT DOCUMENTS

| CN | 1364468 A | 8/2002 | |
|---|---|---|---|
| CN | 1994460 A | 7/2007 | |
| CN | 101069721 A | 11/2007 | |
| CN | 100361705 C | 1/2008 | |
| JP | 7 324039 | 12/1995 | |
| JP | 2774769 | 7/1998 | |
| JP | 2000327567 A | * 11/2000 | ............. A61K 31/16 |
| JP | 2002 145791 | 5/2002 | |
| JP | 2002 540216 | 11/2002 | |
| JP | 2003 300899 | 10/2003 | |
| JP | 2006 290777 | 10/2006 | |
| JP | 2006 290814 | 10/2006 | |
| JP | 2007-28997 | 2/2007 | |
| WO | 00 78338 | 12/2000 | |
| WO | 00 78339 | 12/2000 | |

OTHER PUBLICATIONS

Definition of prevent, Oxford English Dictionary Online, http://dictionary.oed.com/, accessed online on May 27, 2010.*
Entry for Crohn's disease, WebMD, www.webmd.com, accessed online on Oct. 31, 2012.*
Tateishi et al., J. Gastroenterol., 1997, 32, p. 457-463.*
Satoh et al., Journal of Ethnopharmacology, 2003, 86, p. 37-44.*
Sakata et al., J. Gastroenterol., 1998, 33, p. 828-834.*
Ghisalberti et al., Pharmaceutical Biology, 1998, 36(4), p. 237-279.*
Sato et al., Biol. Pharm. Bull., 2004, 27(11), p. 1875-1877.*
Definition of Crohn's disease, MedlinePlus, http://www.nlm.nih.gov/medlineplus/ency/article/000249.htm, accessed online on Aug. 19, 2014.*
Kim et al., Biochemical and Biophysical Research Communications, 1992, 189(2), p. 670-676.*
Xia et al., J. Thorac. Cardiovasc. Surg., 2005, 130, p. 258-264.*
Hashimoto et al., Journal of Ethnopharmacology, 2003, 84, p. 115-119.*
English Espacenet machine translation of JP 2000-327567, http://translationportal.epo.org, accessed online on Apr. 6, 2015.*
Office Action issued May 8, 2012 in Canadian Application No. 2,715,771.
Extended Search Report issued Apr. 11, 2012 in European Application No. 08720747.8.
Heng Fan, et al., "Effects of four regulating-intestine prescriptions on pathology and ultrastructure of colon tissue in rats with ulcerative colitis", World Journal of Gastroenterology, Jan. 1, 2005, XP55023111, pp. 4800-4806.
Terumasa Hayakawa, et al., "Effects of Dai-kenchu-to on Intestinal Obstruction Following Laparotomy", J. Smooth Muscle Res., vol. 35, No. 2, 1999, XP-000995643, pp. 47-54.
Kono, Toru: "Daicho CGRP Oyobi Sono Juyotai o Hyoteki to shita Daiken Chuto no Chokan Ketsuryu Zoka Sayo", Journal of Japan Surgical Association, vol. 68, p. 370, (2007).
Pin, Murata et al., "The herbal medicine Dai-kenchu-to and one of its active components [6]-shogaol increase intestinal blood flow in rats", Life Sciences, vol. 70, pp. 2061-2070, especially 2063-2065, (2002).
Nisibori, Hideki et al., "Effects of the herbal medicine, Dai-kenchu-to on ileus", Medical Science Digest, vol. 33, No. 3, pp. 753 to 756, particularly, p. 754, (2007).
Shoji, Junzo: "The Elucidation of Traditional Drugs by Scientific Methods", School of Pharmaceutical Sciences, Kampo Medicine, pp. 1-22, vol. 35, No. 1, (1984).

(Continued)

*Primary Examiner* — Jonathan S Lau
(74) *Attorney, Agent, or Firm* — Oblon, McClelland, Maier & Neustadt, L.L.P.

(57) ABSTRACT

It is an object of the invention to discover a substance that effectively increases the production of adrenomedullin, as well as to provide an adrenomedullin production-enhancing agent utilizing this substance. The adrenomedullin production-enhancing agent is characterized by inclusion of a ginsenoside, a sanshool, and/or a shogaol as active ingredients.

13 Claims, 10 Drawing Sheets

(56) References Cited

OTHER PUBLICATIONS

Sugai, Etsuko et al., "Pungent Qualities of Sanshool-Related Compounds Evaluated by a Sensory Test and Activation of Rat TRPV1", Biosci., Biotechnol., Biochem., vol. 69, No. 10, pp. 1951-1957, (2005).

Park, Yong-Dae et al., "Human Acyl-CoA: Cholesterol Acyltransferase Inhibitory Activities of Aliphatic Acid Amides from *Zanthoxylum piperitum* DC." Biological & Pharmacheutical Bulletin, vol. 30, No. 1, pp. 205-207, (Jan. 2007).

Kashiwada, Yoshiki et al., "Amides of the Fruit of *Zanthoxylum* SPP.", Phytochemistry, vol. 44, No. 6, pp. 1125-1127, (1997).

Banno, Kazuo et al., "A New Synthesis of the Pungent Principles of Ginger Zingerone, Gingerol and Shogaol", Bulletin of the Chemical Society of Japan, vol. 49, No. 5, pp. 1453-1454, (May 1976).

* cited by examiner

**P<0.01, *P<0.05 VS.TJ-100 900 mg/kg group

Photographs of the large intestine on the 3rd day after enteritis induction
(the upper part is on the anal side)

ADRENOMEDULLIN PRODUCTION ENHANCER

TECHNICAL FIELD

The present invention relates to an adrenomedullin production-enhancing agent, and more particularly to an adrenomedullin production-enhancing agent that is effective in preventing and treating diseases such as Crohn's disease by promoting the production of adrenomedullin, an intestinal peptide which increases blood flow and has anti-inflammatory effects.

BACKGROUND ART

Adrenomedullin was discovered in 1993 as a peptide involved in regulation of the circulatory system with strong vasodilatory effects (Patent Document 1). Adrenomedullin is produced by a variety of organs such as those of the circulatory system and the digestive system, and has important physiological effects such as vasodilatation, neovascularization, antibacterial effects, anti-enteritic effects, protection of the gastric mucosa, and suppression of thrombus formation. Administration of adrenomedullin has correspondingly been confirmed to be effective in the treatment of various diseases, and has been reported to be effective against conditions including myocardial disorders, non-bacterial inflammatory diseases, pulmonary hypertension, bone disorders, myometrial contraction, urinary disorders, and the like (Patent Documents 2 to 7).

However, since adrenomedullin is a peptide, formulation of it is associated with high costs of production, and in the case of direct administration of adrenomedullin, a dosage form such as an injectable preparation or an intravenous drip preparation must be used. Rigorous production technology and management excluding incorporation of foreign matter, such as endotoxin, is thus required. Furthermore, since adrenomedullin has a half-life in blood of only tens of minutes, administration of significant amounts is required for exertion of its effects. However, intravenous administration of a large amount of adrenomedullin may induce hypotension. Moreover, when exposure of specific organs to adrenomedullin is expected, various problems may exist, such as the need for targeting technologies. There has thus been a need for a highly safe medicament which can be produced at low cost and that is when orally administered capable of enhancing activity of the adrenomedullin production system, which is constitutively activated in vivo. However, no such medicament has been available.

Patent Document 1: Japanese Patent No. 2774769
Patent Document 2: WO 00/078338
Patent Document 3: WO 00/078339
Patent Document 4: JP-T-2002-540216
Patent Document 5: JP-A-2003-300899
Patent Document 6: JP-A-2006-290777
Patent Document 7: JP-A-2006-290814

SUMMARY OF THE INVENTION

It is thus an object of the present invention to determine a substance that can be orally administered and that effectively enhances the production of adrenomedullin in vivo, and in addition to provide an adrenomedullin production-enhancing agent utilizing this substance.

DETAILED DESCRIPTION OF THE INVENTION

Figure 1:
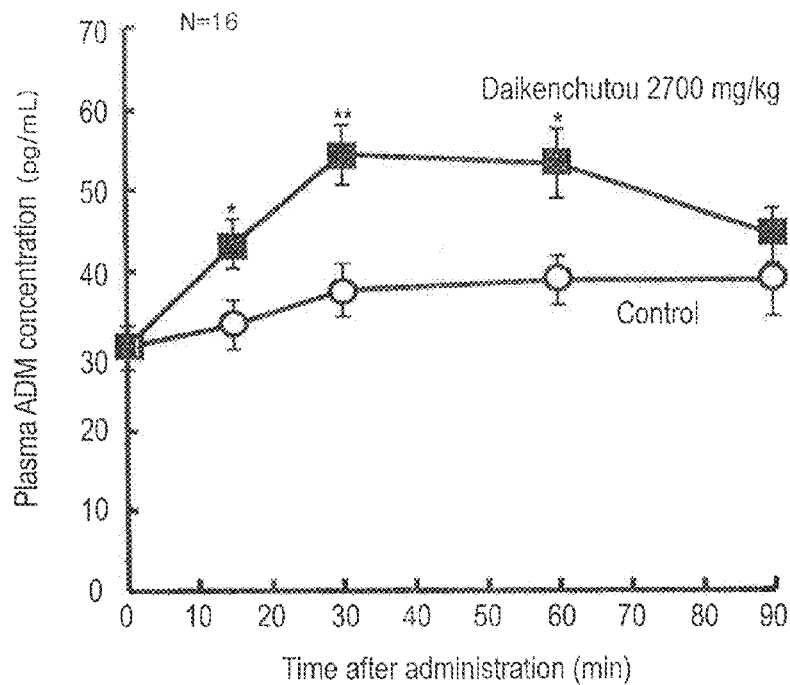
FIG. 1 is a diagram showing the results of measurement of adrenomedullin concentration in plasma of portal vein blood obtained as described in Example 1. Furthermore, * indicates a risk rate of 5% or less, while ** indicates a risk rate of 1% or less.
Figure 2:
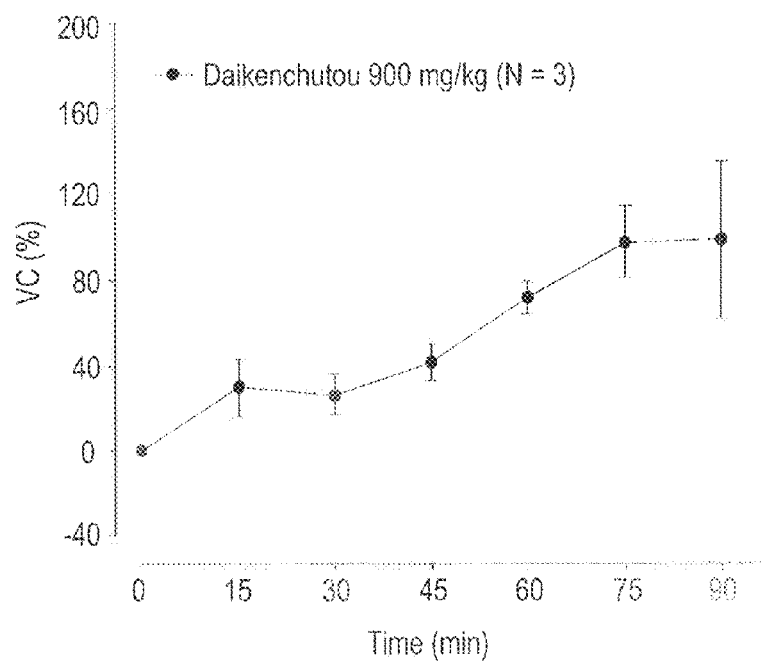
FIG. 2 is a diagram showing the rates of increase in VC as a result of administration of Daikenchutou in Example 2.
Figure 3:
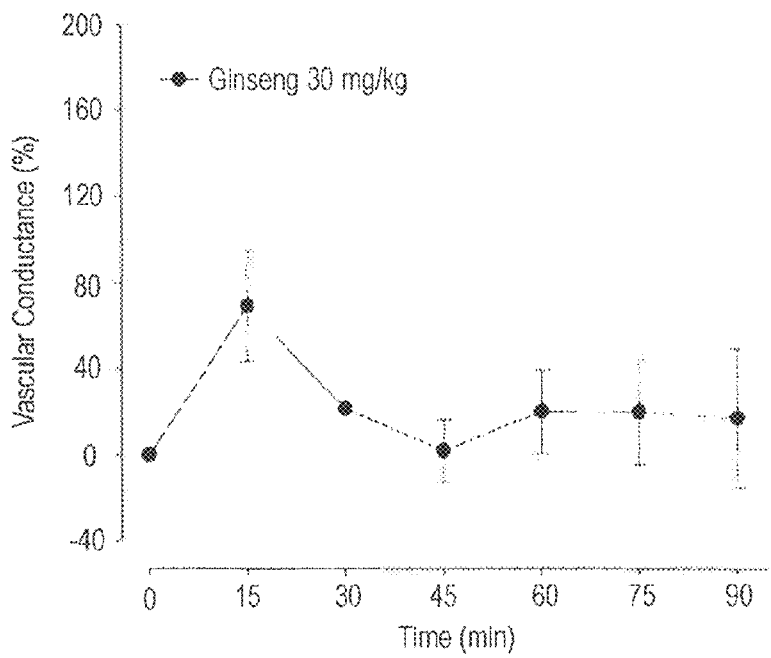
FIG. 3 is a diagram showing the rates of increase in VC as a result of administration of ginseng in Example 2.
Figure 4:
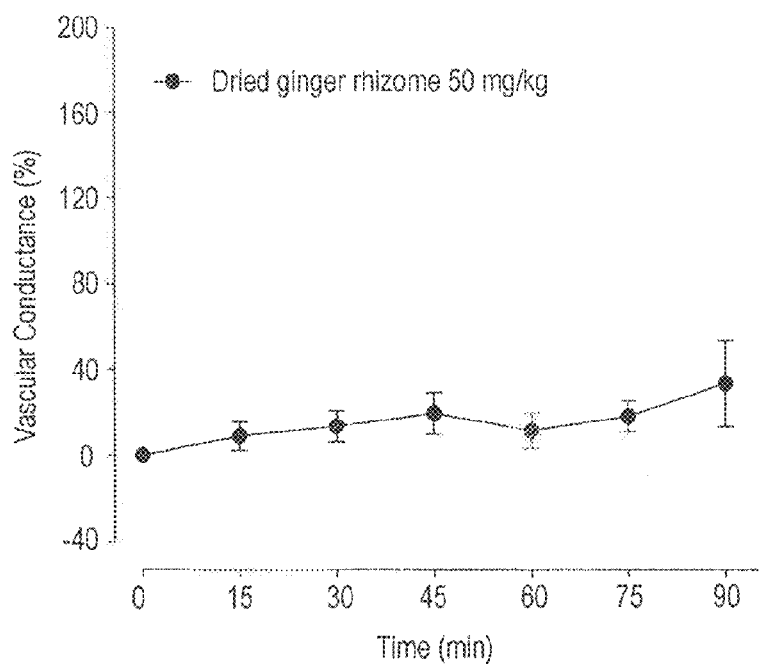
FIG. 4 is a diagram showing the rates of increase in VC as a result of administration of dried ginger rhizome in Example 2.
Figure 5:
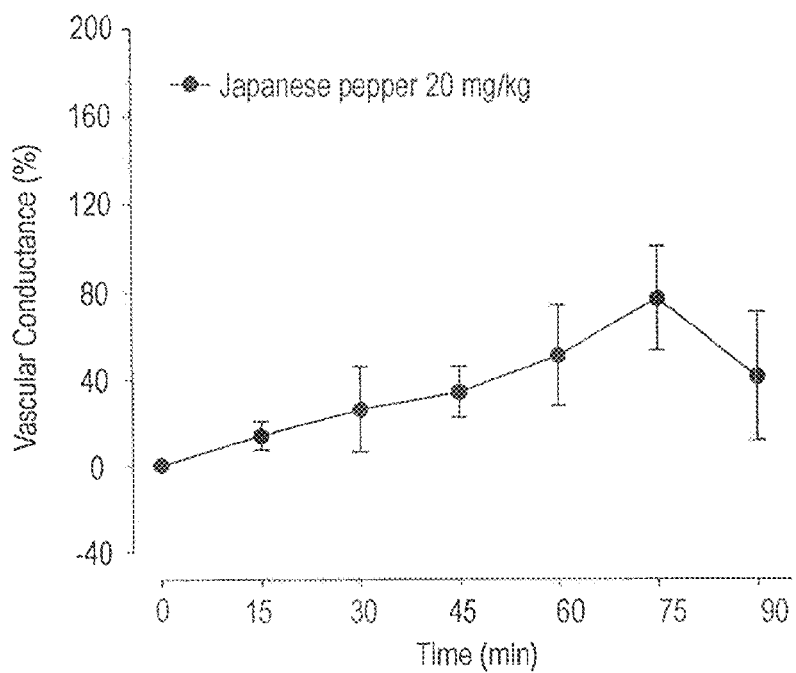
FIG. 5 is a diagram showing the rates of increase in VC as a result of administration of Japanese pepper in Example 2.
Figure 6:
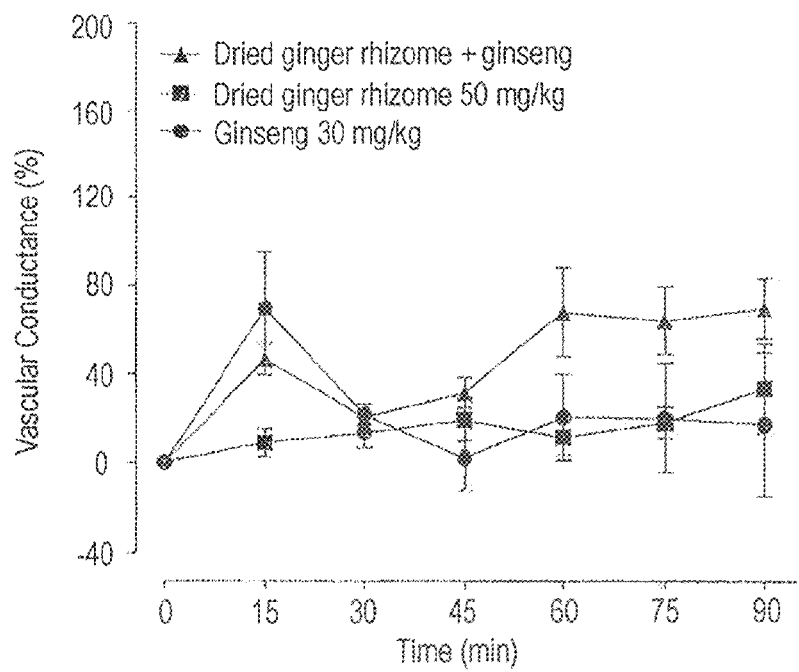
FIG. 6 is a diagram showing the rates of increase in VC as a result of administration of dried ginger rhizome and ginseng in Example 2.
Figure 7:
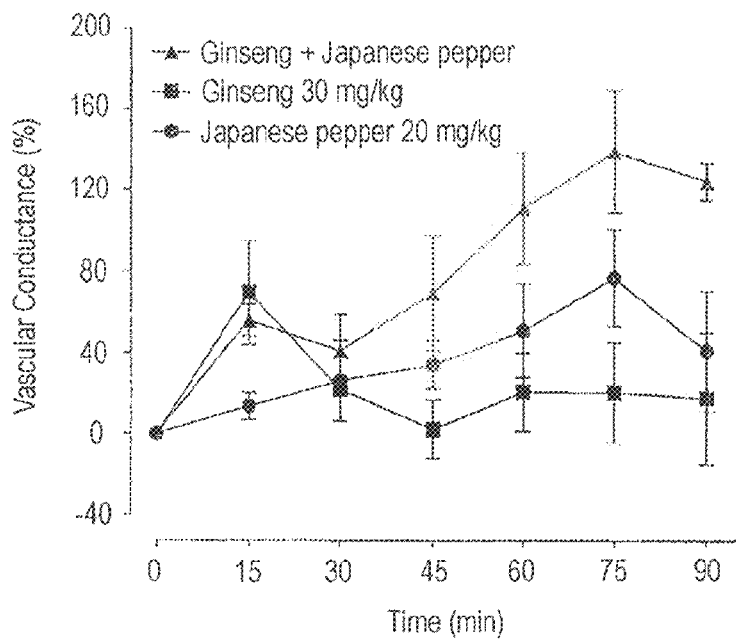
FIG. 7 is a diagram showing the rates of increase in VC as a result of administration of ginseng and Japanese pepper in Example 2.
Figure 8:
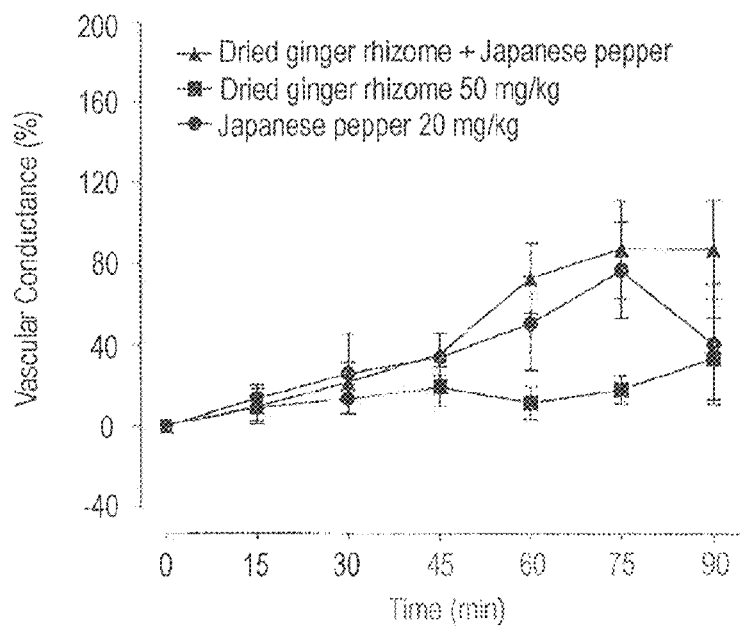
FIG. 8 is a diagram showing the rates of increase in VC as a result of administration of dried ginger rhizome and Japanese pepper in Example 2.

In an attempt to solve the above-described problems, the inventors of the present invention have searched extensively for substances which enhance adrenomedullin production, and have found that an excellent adrenomedullin production-enhancing effect is obtained by combining specific compounds that are contained in known crude drugs, thus eventually completing the invention.

Specifically, the present invention is an adrenomedullin production-enhancing agent containing, as active ingredients, a compound represented by the following formula (1):

(1)

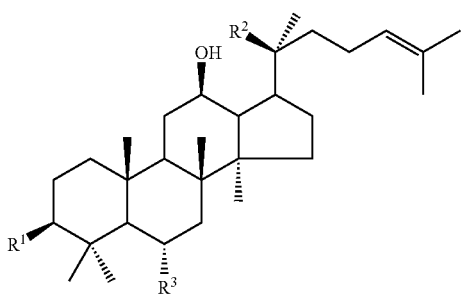

wherein $R^1$, $R^2$, and $R^3$, which may be identical or different, each represent a hydrogen atom, a hydroxyl group, —O-Glc, —O-Glc-Glc, —O-Glc-Ara, or —O-Glc-Rha, provided that Glc represents a glucose residue, Ara an arabinose residue, and Rha a rhamnose residue; and a compound represented by the following formula (2) and/or a compound represented by formula (3):

(2)

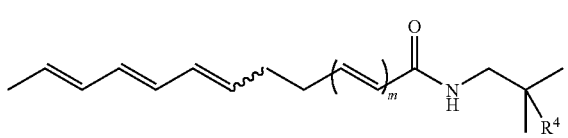

wherein $R^4$ represents a hydrogen atom or a hydroxyl group; m is 1 or 2; and the wavy line indicates whether the part is in the Z- or E-configuration;

(3)

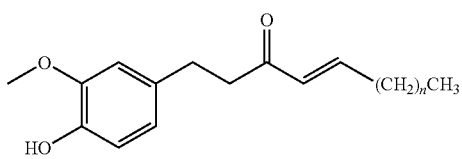

wherein n is 4, 6, or 8.

EFFECTS OF THE INVENTION

The adrenomedullin production-enhancing agent of the invention effectively promotes the production of adrenomedullin, which has various physiological effects including increasing blood flow as well as anti-inflammatory effects. The adrenomedullin production-enhancing agent of the invention can thus be used in the treatment of various diseases. For example, by increasing the amount of blood flow inside the intestinal tract, Crohn's disease, an ischemic disease of the digestive system, and the like can be effectively prevented or treated by it. Furthermore, since the adrenomedullin production-enhancing agent originates from natural substances and can be orally administered, it is very safe, exhibits excellent sustainability of effects, and strongly enhances adrenomedullin production, particularly in the digestive tract.

BEST MODE FOR CARRYING OUT THE INVENTION

As an active ingredient of the adrenomedullin production-enhancing agent of the invention, a compound represented by the following formula (1) (hereinafter, may be referred to as "compound (1)") is used:

(1)

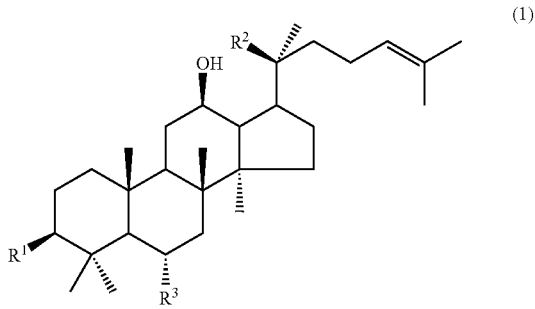

wherein $R^1$, $R^2$, and $R^3$, which may be identical or different, each represent a hydrogen atom, a hydroxyl group, —O-Glc, —O-Glc-Glc, —O-Glc-Ara, or —O-Glc-Rha, provided that Glc represents a glucose residue, Ara an arabinose residue, and Rha a rhamnose residue.

Concerning compound (1), specifically, there may be mentioned ginsenosides such as ginsenoside $Rb_1$, in which $R^1$ and $R^2$ are each —O-Glc-Glc and $R^3$ is a hydrogen atom; ginsenoside $Rb_2$ or Rc, in which $R^1$ is —O-Glc-Glc, $R^2$ is —O-Glc-Ara, and $R^3$ is a hydrogen atom; ginsenoside Rd, in which $R^1$ is —O-Glc-Glc, $R^2$ is —O-Glc, and $R^3$ is a hydrogen atom; ginsenoside Re, in which $R^1$ is a hydroxyl group, $R^2$ is —O-Glc, and $R^3$ is —O-Glc-Rha; ginsenoside $Rg_1$, in which $R^1$ is a hydroxyl group, $R^2$ is —O-Glc, and $R^3$ is —O-Glc; ginsenoside $Rg_2$, in which $R^1$ and $R^2$ are each a hydroxyl group and $R^3$ is —O-Glc-Rha; and ginsenoside $Rh_1$, in which $R^1$ and $R^2$ are each a hydroxyl group and $R^3$ is —O-Glc. Among these, ginsenoside and ginsenoside $Rg_1$ are preferred.

These compounds can be isolated by known methods (document: Kampo Medicine, Vol. 35, No. 1, Pages 1-22 (1984), and the like), or commercially available products can be used.

Furthermore, the adrenomedullin production-enhancing agent of the invention uses the above-described compound represented by formula (1), in combination with a compound represented by the following formula (2) (hereinafter, may be referred to as "compound (2)") and/or a compound represented by formula (3) (hereinafter, may be referred to as "compound (3)").

(2)

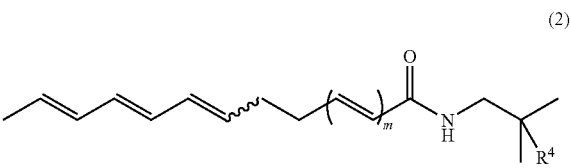

wherein $R^4$ represents a hydrogen atom or a hydroxyl group, m is 1 or 2, and the wavy line indicates whether the part is in the Z- or E-configuration;

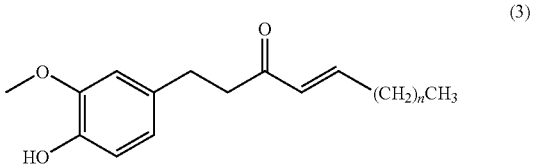

(3)

wherein n is 4, 6, or 8.

Concerning compound (2), specifically, there may be mentioned sanshools such as α-sanshool, in which $R^4$ is a hydrogen atom, m=1, and the wavy line is in the Z-configuration; β-sanshool, in which $R^4$ is a hydrogen atom, m=1, and the wavy line is in the E-configuration; γ-sanshool, in which $R^4$ is a hydrogen atom, m=2, and the wavy line is in the Z-configuration; hydroxy-α-sanshool, in which $R^4$ is a hydroxyl group, m=1, and the wavy line is in the Z-configuration; hydroxy-β-sanshool, in which $R^4$ is a hydroxyl group, m=1, and the wavy line is in the E-configuration; and hydroxy-γ-sanshool, in which $R^4$ is a hydroxyl group, m=2, and the wavy line is in the Z-configuration. Among these, hydroxy-α-sanshool and hydroxy-β-sanshool are preferred.

These compounds can be isolated or synthesized by known methods (document: Biosci Biotechnol Biochem: Vol. 69, No. 10, 1951-1957 (2005); Biological & Pharmaceutical Bulletin (2007), 30(1), 205-207; Phytochemistry (1997), 44(6), 1125-1127; and the like).

On the other hand, concerning compound (3), specifically, 6-shogaol, 8-shogaol, 10-shogaol, and the like may be mentioned. Among these, 6-shogaol is preferred.

These compounds can be isolated or synthesized by known methods (document: Bulletin of the Chemical Society of Japan (1976), 49(5), 1453-1454; Japanese Patent Application No. 63-137843; and the like), or commercially available products can be used.

The adrenomedullin production-enhancing agent of the invention can be produced using the compound represented by formula (1) and the compound represented by formula (2) and/or the compound represented by formula (3) as active ingredients, appropriately mixing these compounds with other pharmaceutical carriers, and formulating this mixture into an oral or a parenteral preparation.

Oral preparations in the form of dust, powders, granules, tablets, capsules, soft capsules, liquids, and the like can be formulated, and pharmaceutical carriers adequate for these, for example starch, lactose, sucrose, mannite, carboxymethylcellulose, corn starch, inorganic salts, and the like, can be used. Upon production of an oral preparation, a binder, a disintegrant, a surfactant, a lubricating agent, a fluidity-promoting agent, a flavoring agent, a colorant, a fragrance, and the like may be incorporated.

Furthermore, parenteral preparations can also be produced according to conventional methods, and distilled water for injection, physiological saline, aqueous glucose solution, plant oil for injection, sesame oil, peanut oil, soybean oil, corn oil, propylene glycol, polyethylene glycol, and the like can generally be used as diluents. If necessary, a bactericidal agent, a preservative, a stabilizer, and the like can be further added.

In regard to the adrenomedullin production-enhancing agent of the invention, the amount of compound (1) to be incorporated as an active ingredient varies with the type of compound, disease to be treated, severity of the disease, age of the patient, and the like, though, for example, in the case of use of ginsenoside $Rb_1$, the amount to be incorporated is about 1 mg to 1 g as a daily dose for an adult. In the case of use of compound (2) as the component in combination with compound (1), the amount to be incorporated is about 1 mg to 1 g as a daily dose for an adult. In the case of use of compound (3) as the component in combination with compound (1), the amount to be incorporated is about 1 mg to 1 g as a daily dose for an adult. On the other hand, in the case of use of compound (2) and compound (3) in combination, the amount to be incorporated is about 2 mg to 2 g in total.

In regard to the adrenomedullin production-enhancing agent of the invention, it is also possible to use a crude drug containing compound (1), and a crude drug containing compound (2) and/or a crude drug containing compound (3) as active ingredients. As a crude-drug containing compound (1), ginseng may be mentioned. As a crude drug containing compound (2), Japanese pepper (Sansho) may be mentioned, and as a crude drug containing compound (3), dried ginger rhizome (Kankyo) may be mentioned. Ginseng, Japanese pepper, and dried ginger rhizome are all materials known as Kampo medicine ingredients, and commercially available products can also be used.

Preparation of the adrenomedullin production-enhancing agent of the invention is carried out by chopping or pulverizing the aforementioned ginseng, and Japanese pepper and/or dried ginger rhizome, separately, and then mixing them uniformly, or if necessary by drying an extract obtained from the materials with an appropriate solvent, and then mixing the resulting product with *Saccharum granorum* as necessary.

The amount of ginseng to be incorporated in the adrenomedullin production-enhancing agent of the invention is about 1 mg to 1 g as a daily dose for an adult. In the case of use of Japanese pepper as the component in combination with ginseng, the amount to be incorporated is about 1 mg to 1 g, and in the case of use of dried ginger rhizome, the amount to be incorporated is about 1 mg to 1 g. On the other hand, in the case of use of Japanese pepper and dried ginger rhizome in combination, the amount to be incorporated is about 2 mg to 2 g in total.

Examples of Kampo medicine prescriptions containing ginseng and Japanese pepper and/or dried ginger rhizome include Daikenchutou, Toukitou, Hangeshashintou, Ninjintou, Hangebyakujyutsutenmatou, Hochuekkitou, Keishinninjintou, Daiboufutou, Ourentou, and the like, and these can also be used as active ingredients for the adrenomedullin production-enhancing agent of the invention. Taking the general constitution of Daikenchutou as an example, 15 g of Daikenchutou contains 1.25 g of a dried extract of mixed crude drugs in proportions of dried ginger rhizome:ginseng:Japanese pepper=5:3:2 (powdered Daikenchutou extract), and 10 g of *Saccharum granorum*.

The adrenomedullin production-enhancing agent of the invention can be produced using the aforementioned ginseng and dried ginger rhizome and/or Japanese pepper as active ingredients, mixing them with other pharmaceutical carriers, and formulating the mixture obtained into an oral or a parenteral preparation. The same components as described above can be used as pharmaceutical carriers.

When the adrenomedullin production-enhancing agent of the invention that is obtainable as described above is administered, adrenomedullin production by various organs and tissues is promoted. Since adrenomedullin has various physiological effects, such as vasodilatation, neovascularization, antibacterial activity, anti-enteritic effects, protection of the gastric mucosa, and suppression of thrombus formation, it is effective in the prevention and treatment of diseases including inflammatory bowel diseases such as ulcerative colitis and Crohn's disease, urinary disorders, myometrial contraction, bone disorders, hypertension, myocardial disorders, non-bacterial inflammatory diseases, and hepatitis.

EXAMPLES

Hereinafter, the present invention will be explained in greater detail by way of Examples, though the invention is not at all intended to be limited to these Examples. In the Examples, a powdered extract obtained by extracting crude drug or a mixture of crude drugs with water according to a conventional method was used.

Example 1

Adrenomedullin Production-Enhancing Effect of Daikenchutou

Male SD rats (8 to 10 weeks of age, body weight 300 to 400 g) were used (n=16). *Saccharum granorum* was added to distilled water to a concentration of 480 mg/mL to prepare an aqueous solution of it. To this aqueous solution of *Saccharum granorum*, a powdered extract of Daikenchutou was added to a concentration of 60 mg/mL, by weighing immediately at the time of use, and the mixture was homogeneously dispersed by stirring for 30 minutes at room temperature for use as a test specimen. A 5 mL/kg portion of the test specimen, which had been kept warm at 37° C., was administered into the duodenum through a cannula, and blood was collected from the portal vein at 0, 15, 30, 60, and 90 minutes after administration. A control group was administered distilled water in the same fashion. Approximately 5 mL of the portal vein blood was inserted into a 15-mL centrifuge tube made of polypropylene (PP), in which an ethylenediaminetetraacetic acid (EDTA)/aprotinin solution (containing 5 mg of EDTA-2Na and 2500 KIU of aprotinin) had been dispensed in an amount of 100 μL, and centrifugation was performed at 1500 g at 4° C. for 15 minutes. Two mL of blood plasma and 0.16 mL of an acidified solution having the following composition were added to a 5-mL centrifuge tube made of PP for high-speed centrifuge to acidify the plasma sample.

The supernatant obtained by centrifugation at 7000 g at 4° C. for 20 minutes was passed through an activated Sep-Pak cartridge column (C-18 column, WAT020805 manufactured by Waters Corp.), and adrenomedullin (ADM) was adsorbed to the column. The column was washed twice with 2.5 mL of a column washing liquid (0.1% aqueous solution of trifluoroacetic acid (TFA)), and the adsorbed ADM was then eluted with 2 mL of a column eluent (0.1% TFA methanol solution). The eluate was received into a 5-mL centrifuge tube and subjected to centrifugation under reduced pressure to evaporate and dry it to a solid. The dried sample was stored at −80° C. until EIA (Enzyme immunoassay) measurement. Quantification of ADM was carried out using a Rat ADM EIA kit (EK-010-08, manufactured by Phoenix Pharmaceuticals, Inc.). The evaporated and dried solid sample was dissolved in 400 μL of an EIA buffer solution, and the solution was heated at 90° C. for 15 minutes and then centrifuged at 2000 g for 20 minutes. The resulting supernatant was used as the EIA sample. Data are expressed as the mean value±standard error (S.E.M.), and were subjected to two-way ANOVA and then to Dunnett's multiple comparison test or Student's t-test. A risk rate of 5% or less was employed as the significance level. Changes in ADM concentration in blood plasma are presented in Table 1 and FIG. 1.

| (Composition of acidified solution) | | |
|---|---|---|
| NaCl | 100 mg | (final concentration: 1%) |
| Trifluoroacetic acid (TFA) | 0.1 mL | (final concentration: 1%) |
| Formic acid | 0.5 mL | (final concentration: 5%) |
| 1N hydrochloric acid | 8.0 mL | (final concentration: 80%) |
| Distilled water | 1.4 mL | |
| Total: | 10 mL | |

TABLE 1

| | | ADM concentration (pg/mL) | | | | |
|---|---|---|---|---|---|---|
| | | 0 min | 15 min | 30 min | 60 min | 90 min |
| Control | Mean value | 30.4 | 33.2 | 37.4 | 38.7 | 38.6 |
| | Standard error | 2.7 | 3.0 | 3.3 | 3.0 | 4.6 |
| Daikenchutou | Mean value | 30.4 | 43.3 | 54.3 | 53.0 | 44.1 |
| | Standard error | 2.7 | 3.0 | 3.7 | 4.4 | 3.3 |

While the ADM concentration in plasma of portal vein blood recovered immediately before enteric injection of the test specimen was 30.4±2.7 pg/mL, the ADM concentrations for recovery at 15, 30, 60, and 90 minutes after administration of the test specimen Daikenchutou were 43.3±3.0, 54.3±3.7, 53.0±4.4, and 44.1±3.3 pg/mL, respectively, and significantly increased over time. In a comparison between the group administered distilled water and that administered Daikenchutou, significant differences in ADM concentration ($p<0.01$) were confirmed at 15, 30, and 60 minutes after administration.

Example 2

Blood Flow-Increasing Effects of Daikenchutou and its Constituent Crude Drugs

Male SD rats (9 to 11 weeks of age, body weight 260 to 350 g) were used (n=3 or 6). *Saccharum granorum* and a powdered extract of Daikenchutou were suspended in distilled water to obtain a concentration of 160 mg/mL of *Saccharum granorum* and to a concentration of 20 mg/mL for the powdered extract of Daikenchutou, and the suspension was used as a test specimen (Daikenchutou). Furthermore, test specimens respectively containing the individual crude drugs were prepared by adding the ginseng extract powder, dried ginger rhizome extract powder, and Japanese pepper extract powder to distilled water to obtain concentrations of 6 mg/mL, 10 mg/mL, and 4 mg/mL, respectively. Furthermore, test specimens containing two crude drugs among the aforementioned three crude drugs in combination were prepared by addition to distilled water to obtain concentrations of 6 mg/mL for the ginseng extract powder and 10 mg/mL for the dried ginger rhizome extract powder, 6 mg/mL for the ginseng extract powder and 4 mg/mL for the Japanese pepper extract powder, or 4 mg/mL of the Japanese pepper extract powder and 10 mg/mL of the dried ginger rhizome extract powder. After preliminarily placing an 18 G Surflo indwelling needle inserted through the caecum, 5 mL/kg portions of test specimens which had been kept warm at 37° C. were administered into the colon 0.5 to 1 hour later, by which time baseline blood flow had stabilized.

A polyethylene tube with an inner diameter of 0.58 mm was inserted through the left common carotid artery of an anesthetized rat, and the tip was left indwelling in the left ventricle. A tracheal cannula was placed indwelling in the trachea and then connected to a respirator (SN-480-7, manufactured by Shinano Seisakusho Co., Ltd.); artificial respiration was then performed at a frequency of 60 RPM. Body temperature was maintained at 37±0.5° C. by a temperature controller (NS-TC10, manufactured by Neuroscience, Inc.). The rat was incised along the midline of the abdomen, the caecum was taken outside the body, and then the distal colon was exteriorized. The lower part of the colon was lightly lifted with forceps, and with the feces still present inside the colon, four sites were tied and fixed to the end of the incised right and left rectus abdominis with 5-0 suture, such that the length between the tied sites was 1 cm. A blood flow probe was positioned at the upper part of the fixed distal colon, and blood flow (flow, mass, velocity) was measured using a laser tissue blood flow meter (ALF21N, manufactured by Advance Co., Ltd.). To prevent drying, the entire abdomen including the blood flow probe was covered with plastic wrap. In addition, monitoring of blood pressure and heart rate was carried out simultaneously with amount of blood flow, and the respective results of measurement were recorded with data analysis software (Chart V3.6 [v5.4.2], manufactured by ADInstruments Corp.) via a patient monitoring apparatus (BP-508, manufactured by Colin Corp.) [biological amplifier (Nihon Kohden Corp.)] and a data recording apparatus (Power Lab/800[8/30], manufactured by ADInstruments Corp.). The blood flow measurement was continued until 90 minutes after drug administration, vascular conductance (VC) obtained by dividing flow by blood pressure was employed as an index for blood flow, and the rate of increase (%) in VC was calculated. The rates of increase in VC for the respective test specimens are presented in Table 2 and FIGS. 2 to 8.

The group administered Daikenchutou exhibited an increase in VC at 15 to 90 minutes after administration. Among the groups administered individual constituent crude drugs of Daikenchutou, that administered ginseng exhibited a temporary increase in blood flow at 15 minutes after administration, and the group administered Japanese pepper exhibited a weak increase, with a peak at 75 minutes after administration. Dried ginger rhizome did not clearly increase blood flow. Among the combinations of constituent crude drugs, that of ginseng with dried ginger rhizome and that of ginseng with Japanese pepper yielded clearly higher increases in VC than administrations of the individual components alone. No change in the rate of increase was observed with combined use of dried ginger rhizome and Japanese pepper.

Example 3

Effect of ADM Antagonist Pretreatment on the Blood Flow-Increasing Effect of Daikenchutou Male SD rats were divided into two groups: a Daikenchutou-treated group and an ADM antagonist-pretreated group (n=7 or 8). A solution with a 160 mg/mL concentration of *Saccharum granorum* was prepared using distilled water, and powdered Daikenchutou extract was weighed at the time of use to obtain a concentration of 20 mg/mL and homogeneously dispersed in the same solution by stirring at room temperature for 30 minutes or longer to obtain Daikenchutou (TJ-100). This was administered into the colon in the Daikenchutou-treated group in an amount of 900 mg/5 mL/kg. On the other hand, for the ADM antagonist-pretreated group, a human ADM antagonist (h. ADM22-52, 4302-v, manufactured by Peptide Institute, Inc.) was dissolved in physiological saline at 30 μmol/L, and the solution was intravenously administered through a cannula placed under anesthesia, at a

TABLE 2

Rates of increase in VC for respective test specimens

| Test specimen (mg/kg) | | VC (%) | | | | | |
|---|---|---|---|---|---|---|---|
| | | 15 min | 30 min | 45 min | 60 min | 75 min | 90 min |
| Daikenchutou (900) | Mean value | 30.23 | 26.51 | 42.70 | 73.33 | 99.00 | 100.86 |
| | Standard error | 13.83 | 9.00 | 8.42 | 7.77 | 15.93 | 36.45 |
| Ginseng (30) | Mean value | 69.37 | 21.85 | 2.03 | 20.50 | 20.23 | 17.40 |
| | Standard error | 25.67 | 3.49 | 14.61 | 19.39 | 24.58 | 32.38 |
| Dried ginger rhizome (50) | Mean value | 8.84 | 13.42 | 19.51 | 11.51 | 18.22 | 33.42 |
| | Standard error | 6.56 | 6.96 | 9.72 | 8.18 | 7.06 | 20.07 |
| Japanese pepper (20) | Mean value | 13.55 | 25.84 | 33.95 | 50.65 | 76.63 | 40.80 |
| | Standard error | 6.72 | 19.94 | 11.81 | 23.06 | 23.71 | 29.70 |
| Ginseng (30) Dried ginger rhizome (50) | Mean value | 46.57 | 20.67 | 31.65 | 67.86 | 64.13 | 69.72 |
| | Standard error | 6.95 | 5.93 | 6.94 | 20.12 | 15.48 | 13.80 |
| Ginseng (30) Japanese pepper (20) | Mean value | 55.89 | 40.74 | 69.16 | 111.18 | 139.12 | 124.43 |
| | Standard error | 7.91 | 17.89 | 28.20 | 27.69 | 30.45 | 9.36 |
| Dried ginger rhizome (50) Japanese pepper (20) | Mean value | 9.60 | 21.56 | 35.76 | 72.89 | 87.30 | 87.48 |
| | Standard error | 8.85 | 9.68 | 10.19 | 17.21 | 24.34 | 24.21 | dose of 30 nmol/1 mL/kg, and 15 minutes later Daikenchutou was administered into the colon in an amount of 900 mg/5 mL/kg.

Figure 9:
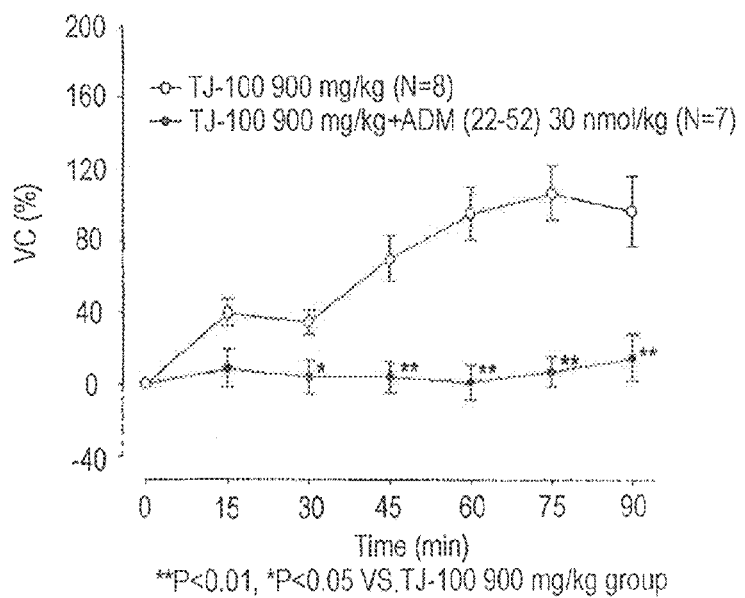
FIG. 9 is a diagram showing the rates of increase in VC in the ADM antagonist-pretreated group and the Daikenchutou-treated group in Example 3.

A polyethylene tube with an inner diameter of 0.8 mm was inserted through the left common carotid artery of an anesthetized rat, and a tip was left indwelling in the left ventricle. A tracheal cannula was placed indwelling in the trachea and connected to a respirator (SN-480-7); artificial respiration was then performed at a frequency of 60 RPM. Body temperature was maintained at 37±0.5° C. by a temperature controller (NS-TC10). The rate of increase in VC (%) was calculated in the same fashion as in Example 2. The rates of increase in VC for the respective groups are presented in Table 3 and FIG. 9. The results of measurement are expressed as the mean value±standard error (S.E.M.). Comparison of effects was performed by one-way analysis of variance (ANOVA), followed by the Scheffe multiple comparison test. A risk rate of 5% or less was employed as the significance level.

$Rb_1$, or ginsenoside $Rg_1$ was added to a 1% aqueous solution of Tween 80 to obtain concentrations of 0.06 mg/mL, 0.2 mg/mL, and 0.2 mg/mL, respectively, and the resulting solutions were used as the respective test specimens for administration of individual crude drug components. Furthermore, test specimens for the administration of hydroxysanshool with a ginseng extract, ginsenoside $Rb_1$, or ginsenoside $Rg_1$ in combination were prepared by adding, to a 1% aqueous solution of Tween 80, hydroxysanshool at a concentration of 0.06 mg/mL, and a powdered ginseng extract, ginsenoside $Rb_1$, or ginsenoside $Rg_1$ at a concentration of 6 mg/mL, 0.2 mg/mL, or 0.2 mg/mL, respectively. After preliminarily placing an 18 G Surflo indwelling needle inserted through the caecum, 5 mL/kg portions of test specimens which had been kept warm at 37° C. were administered into the colon 0.5 to 1 hour later, by which time baseline blood flow had stabilized. A control group was administered a 1% aqueous solution of Tween 80.

TABLE 3

Suppression by ADM antagonist of increase in blood flow by Daikenchutou

| Test specimen | | VC (%) | | | | | |
|---|---|---|---|---|---|---|---|
| | | 15 min | 30 min | 45 min | 60 min | 75 min | 90 min |
| Daikenchutou (900 mg/kg) | Mean value | 39.82 | 34.79 | 70.15 | 95.29 | 106.80 | 96.81 |
| | Standard error | 7.66 | 7.18 | 13.16 | 14.45 | 14.94 | 19.40 |
| Daikenchutou (900 mg/kg) + ADM(22-52) (30 nmol/kg) | Mean value | 8.72 | 4.03 | 4.07 | 1.28 | 7.28 | 15.12 |
| | Standard error | 10.85 | 9.40 | 8.71 | 9.75 | 8.53 | 12.95 |

With ADM antagonist pretreatment, a significant decrease in VC of 30.8 to 99.5% compared to the group administered Daikenchutou alone was found up to 30 to 90 minutes after administration. Since ADM antagonist pretreatment decreased the increase in blood flow induced by Daikenchutou, it was confirmed that ADM has a blood flow-increasing effect.

Example 4

Blood Flow-Increasing Effects of Components in Crude Drugs (1)

Figure 10:
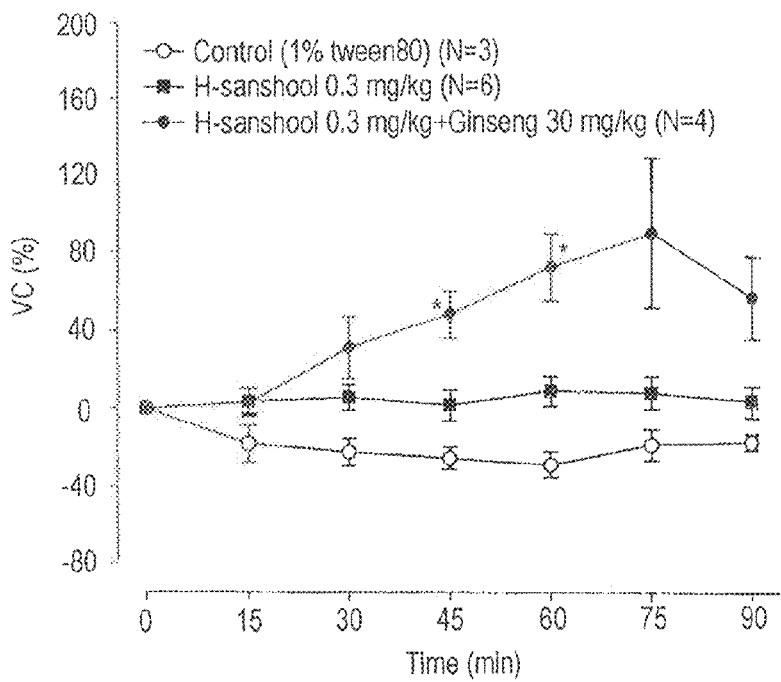
FIG. 10 is a diagram showing the rates of increase in VC as a result of administration of hydroxysanshool alone and combined administration of hydroxysanshool and a ginseng extract in Example 4.
Figure 11:
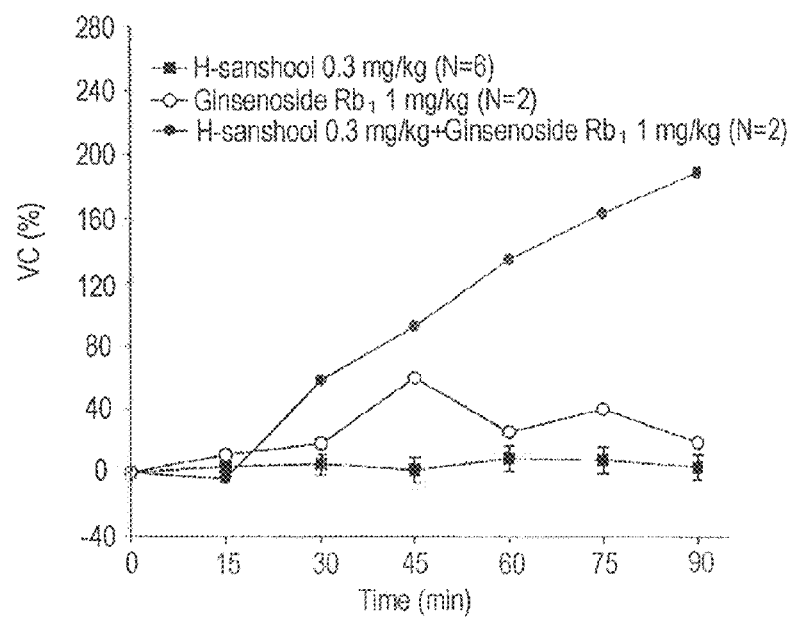
FIG. 11 is a diagram showing the rates of increase in VC as a result of administration of ginsenoside $Rb_1$ alone and combined administration of hydroxysanshool and ginsenoside $Rb_1$ in Example 4.
Figure 12:
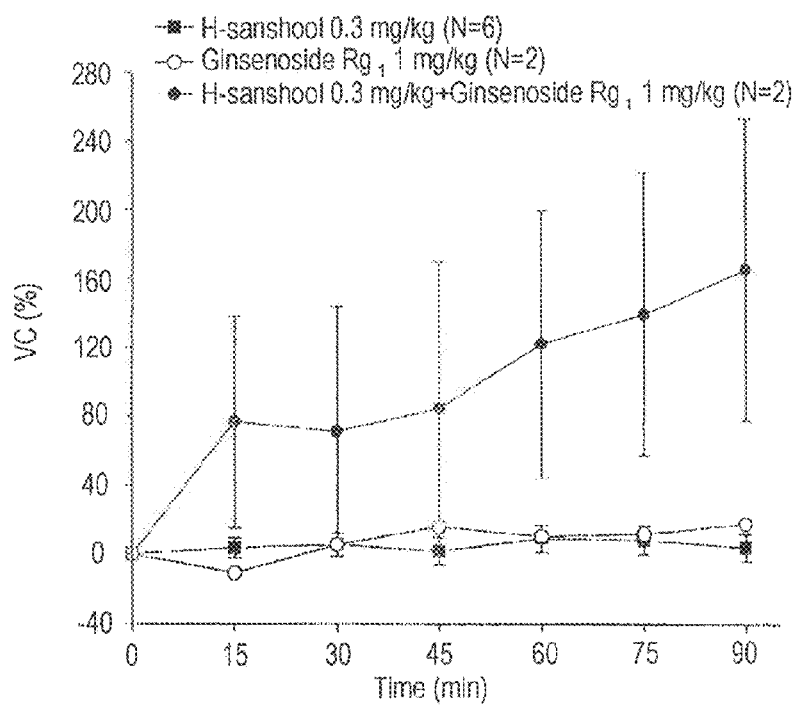
FIG. 12 is a diagram showing the rates of increase in VC as a result of administration of ginsenoside $Rg_1$ alone and combined administration of hydroxysanshool and ginsenoside $Rg_1$ in Example 4.

Male SD rats (8 to 10 weeks of age, body weight 240 to 360 g) were used (n=2 to 6). Hydroxy-β-sanshool, ginsenoside A polyethylene tube with an inner diameter of 0.8 mm was inserted through the left common carotid artery of an anesthetized rat, and the tip was left indwelling in the left ventricle. A tracheal cannula was placed indwelling in the trachea and connected to a respirator (SN-480-7); artificial respiration was then performed at a frequency of 60 RPM. Body temperature was maintained at 37±0.5° C. by a temperature controller (NS-TC10). The rate of increase in VC (%) was calculated in the same fashion as in Example 2. The rates of increase in VC for the respective test specimens are presented in Table 4 and FIGS. 10 to 12. The results of measurement are expressed as the mean value±standard error (S.E.M.). Comparison of effects was performed by one-way analysis of variance (ANOVA), followed by the Scheffe multiple comparison test. A risk rate of 5% or less was employed as the significance level.

TABLE 4

Rates of increase in VC by hydroxysanshool

| Test specimen | | VC (%) | | | | | |
|---|---|---|---|---|---|---|---|
| (mg/kg) | | 15 min | 30 min | 45 min | 60 min | 75 min | 90 min |
| Control | Mean value | −17.77 | −22.20 | −25.23 | −28.48 | −18.04 | −16.61 |
| | Standard error | 9.58 | 7.12 | 5.71 | 6.71 | 8.01 | 4.36 |
| H-sanshool (0.3) | Mean value | 3.89 | 5.79 | 2.09 | 9.46 | 8.58 | 4.19 |
| | Standard error | 6.08 | 6.68 | 8.04 | 7.88 | 8.42 | 8.10 |
| H-sanshool (0.3) | Mean value | 3.41 | 31.49 | 48.67 | 73.02 | 90.97 | 57.58 |

TABLE 4-continued

Rates of increase in VC by hydroxysanshool

| Test specimen (mg/kg) | | VC (%) | | | | | |
|---|---|---|---|---|---|---|---|
| | | 15 min | 30 min | 45 min | 60 min | 75 min | 90 min |
| Ginseng (30) | Standard error | 7.35 | 15.99 | 12.10 | 17.43 | 38.59 | 21.18 |
| Ginsenoside Rb₁ (1) | Mean value | 11.72 | 18.87 | 60.21 | 26.20 | 40.81 | 19.98 |
| | Standard error | 4.36 | 17.59 | 7.74 | 0.00 | 2.68 | 0.39 |
| H-sanshool (0.3) + Ginsenoside Rb₁ (1) | Mean value | −13.97 | 22.26 | 50.64 | 87.81 | 114.10 | 104.80 |
| | Standard error | 17.67 | 39.88 | 37.38 | 34.76 | 29.22 | 50.72 |
| Ginsenoside Rg₁ (1) | Mean value | −10.83 | 5.84 | 16.29 | 10.92 | 12.25 | 18.11 |
| | Standard error | 14.14 | 25.96 | 5.66 | 10.58 | 1.85 | 4.96 |
| H-sanshool (0.3) + Ginsenoside Rg₁ (1) | Mean value | 76.79 | 71.25 | 84.85 | 122.22 | 139.55 | 165.77 |
| | Standard error | 61.48 | 72.71 | 85.25 | 77.74 | 82.35 | 87.90 |

Hydroxysanshool did not increase blood flow when administered alone. However, when used in combination with the ginseng extract, a significant increase in VC of 53.7 to 109.0% was observed compared to the control group up to 30 to 90 minutes after administration. Furthermore, compared with the group administered hydroxysanshool alone, the combination yielded significant increases in VC of 45.4, 63.4, and 46.8%, respectively, at 45, 60, and 90 minutes after administration. In the case of combined use, peak increase appeared at 75 minutes after administration, consistent with the pattern of blood flow increase observed in the case of administration of Daikenchutou in Example and single administration of a Japanese pepper extract. Furthermore, the group administered hydroxysanshool and ginsenoside Rb₁ or Rg₁ in combination also exhibited marked increases in VC compared to the group administered hydroxysanshool alone. These findings indicated that hydroxysanshool functions as an active ingredient of Japanese pepper, and suggested that ginseng plays an important role in expression of the activity of hydroxysanshool.

Example 5

Blood Flow-Increasing Effects of Components in Crude Drugs (2)

Male SD rats (8 to 10 weeks of age) were used. 6-Shogaol was added to a 1% aqueous solution of Tween 80 to obtain a concentration of 0.4 mg/mL, and the resulting solution was used as a test specimen. Furthermore, ginsenoside Rb₁ and 6-shogaol were added to a 1% aqueous solution of Tween 80 at concentrations of 0.2 mg/mL and 0.4 mg/mL, respectively, to prepare test specimens. After preliminarily placing an 18 G Surflo indwelling needle inserted through the caecum, 5 mL/kg portions of test specimens which had been kept warm at 37° C. were administered into the colon 0.5 to 1 hour later, by which time baseline blood flow had stabilized. A control group was administered 1% aqueous solution of Tween 80.

Figure 13:
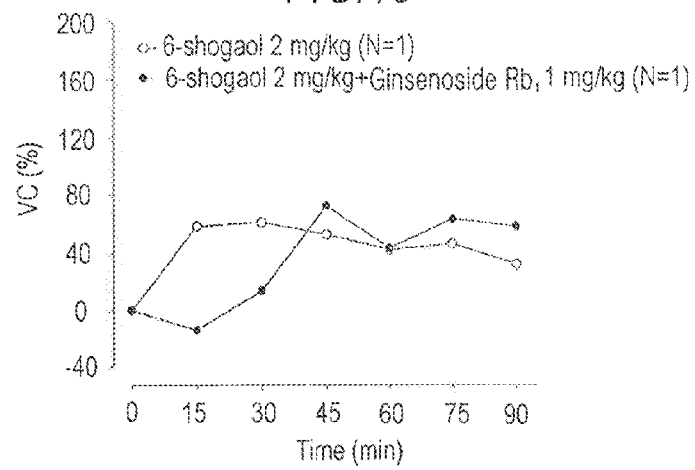
FIG. 13 is a diagram showing the rates of increase in VC as a result of administration of 6-shogaol alone and combined administration of hydroxysanshool and 6-shogaol in Example 5.

A polyethylene tube with an inner diameter of 0.8 mm was inserted through the left common carotid artery of an anesthetized rat, and the tip was left indwelling in the left ventricle. A tracheal cannula was placed indwelling in the trachea and connected to a respirator (SN-480-7); artificial respiration was then performed at a frequency of 60 RPM. Body temperature was maintained at 37±0.5° C. by a temperature controller (NS-TC10). The rate of increase in VC (%) was calculated in the same fashion as in Example 2. The rates of increase in VC for the respective test specimens are presented in Table 5 and FIG. 13.

TABLE 5

| Test specimen (mg/kg) | VC (%) | | | | | |
|---|---|---|---|---|---|---|
| | 15 min | 30 min | 45 min | 60 min | 75 min | 90 min |
| 6-Shogaol (2) | 58.32 | 61.20 | 53.07 | 42.55 | 46.68 | 32.92 |
| 6-Shogaol (2) + Ginsenoside Rb₁ (1) | −14.17 | 13.84 | 72.66 | 43.75 | 63.84 | 58.82 |

6-Shogaol, when administered alone, induced an increase in blood flow from just after administration that peaked at 30 minutes. When used in combination with ginsenoside Rb₁, it yielded an increase in blood flow which peaked at 45 minutes.

Example 6

Anti-Enteritic Effect in an Animal Model of Crohn's Disease

Male BALB/c mice (20 to 25 g) were used (n=6 or 7). *Saccharum granorum* and powdered Daikenchutou extract were added to distilled water to obtain concentrations of 80 mg/mL and 10 mg/mL, respectively, for preparation of the test specimen (Daikenchutou).

2,4,6-Trinitro-benzene sulfonic acid (TNBS, manufactured by Tokyo Chemical Industry Co., Ltd.) was weighed in a tube made of PP, a 50% aqueous solution of EtOH was added to the tube, and the mixture was stirred and dissolved to obtain a concentration of 15 mg/mL. A 1-mL Terumo syringe was connected to a feeding tube (SF-FT0380FG, manufactured by Terumo Corp., Fr3.5, outer diameter 1.2 mm). A position 3.5 cm from a tip of the cannula was marked with an oil marker pen. The mouse was left alone in a small wire mesh cage for 15 to 30 minutes to induce defecation, and anesthesia was performed by peritoneal administration of pentobarbital at 55 mg/kg and atropine at 0.75 mg/kg (manufactured by Sigma-Aldrich Company). An additional 15 to 30 minutes later, a cannula in which TNBS solution had been filled, was slowly inserted to a depth of 3.5 cm after attaching olive oil at the tip (with olive oil added to the tip). With the cannula still inserted, the anus was closed with a paper clip, and the intestinal lumen was sealed. The mouse was suspended in the air, TNBS was slowly infused (2 sec/0.1 mL) in an amount of 1.5 mg/0.1 mL/head, and the mouse was maintained as such for 30 seconds to induce enteritis.

At 8, 24, 32, 48, and 56 hours after the infusion of TNBS, Daikenchutou was forcibly administered orally in an amount of 900 mL/kg. A control group was administered distilled water in the same fashion. The mice were subjected to laparotomy on the third day (72 hours) from the time of induction of enteritis by infusion of TNBS into the intestine, and the presence or absence of adhesions was observed. The portion from the caecum to the anus was collected, and photographs were taken (Digital Camera D100, manufactured by Nikon Corp.). This portion was cut along the longitudinal muscles, its content was washed away with physiological saline, and photographs were taken again, with the mucosal surface facing upward. The photographic images were inputted into image analysis software (Image J), and the area of necrosis (cm$^2$) of the lumen surface was measured. An untreated group which had not been subjected to induction of enteritis and administration of the test specimen was evaluated for disease state in the same fashion.

Figure 14:
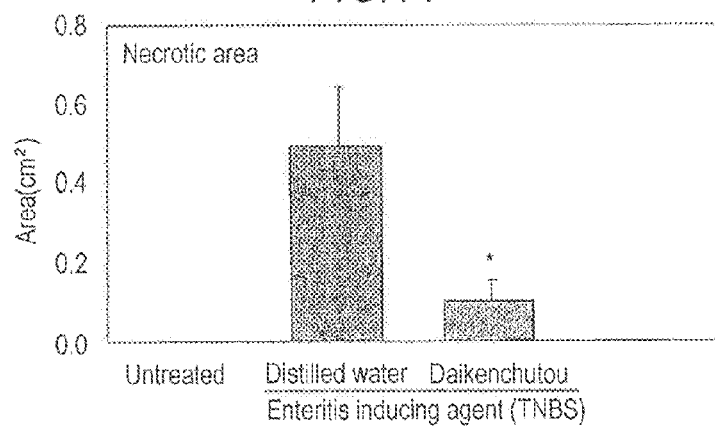
FIG. 14 is a diagram showing the results of measurement of necrotic area in Example 6.
Figure 15:
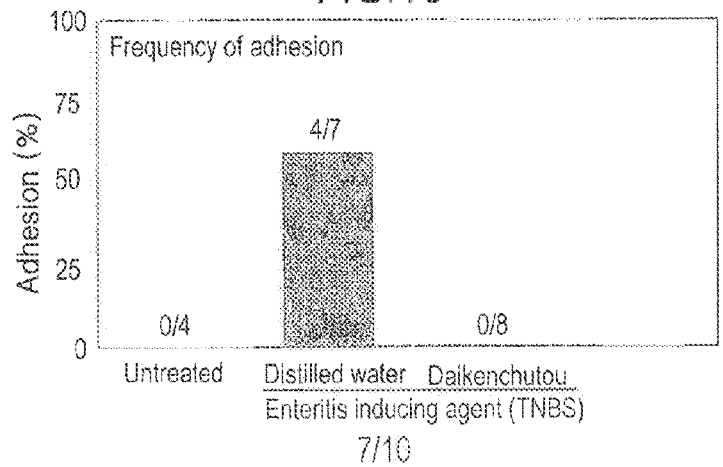
FIG. 15 is a diagram showing the results of measurement of frequency of adhesions in Example 6.
Figure 16:
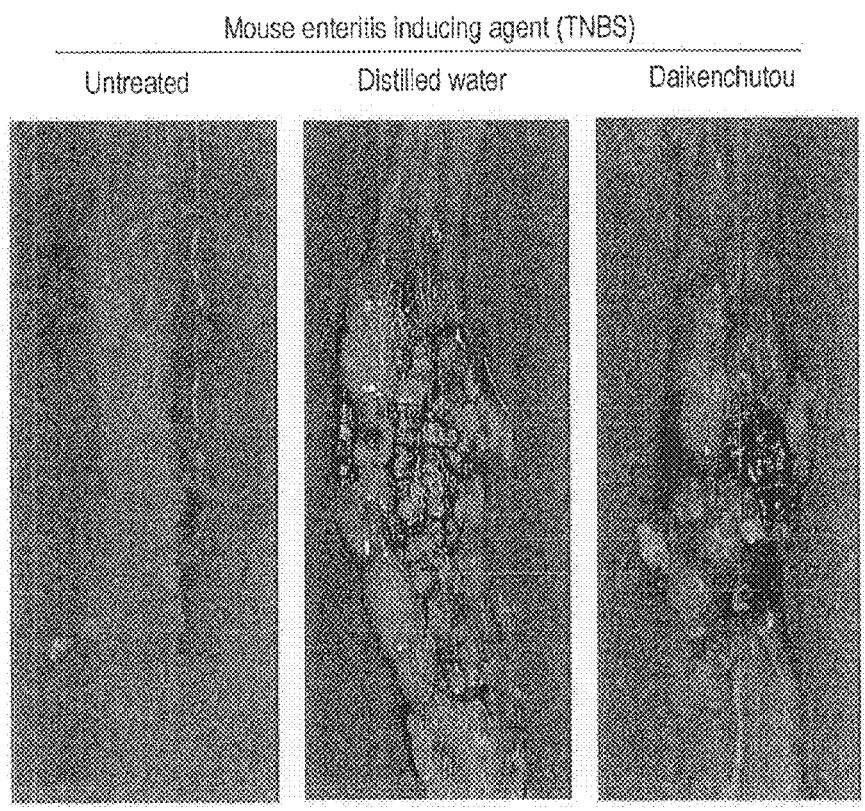
FIG. 16 is a photograph of the large intestine three days after induction of enteritis in Example 6.

Measurements of the area of necrosis were examined for differences between groups by Welch's t-test. A risk rate of 5% or less was employed as the significance level. The results of measurement of area of necrosis are presented in FIG. 14, and the frequency of adhesions is presented in FIG. 15. Furthermore, a photograph of the large intestine at 72 hours after infusion of TNBS into the intestine is presented in FIG. 16.

In the control group, visual evaluation of the large intestine three days after induction of enteritis was performed, and formation of mesenteric adhesions in the large intestine and severe necrosis of the luminal mucosa were observed. On the other hand, in the group administered Daikenchutou five times orally from 8 hours after TNBS treatment, the frequency of adhesions in the large intestine and the area of severe necrosis in the inner lumen were clearly decreased.

Example 7

Effects of Daikenchutou in a Rat Model of Hepatic Cirrhosis

A thioacetamide (TA) solution at a concentration of 300 mg/L was administered by feeding to a male SD rat for 20 weeks to induce hepatic cirrhosis. Powdered Daikenchutou extract was administered by mixing with feed at a dose of 50 or 200 mg/kg/day, from the 10th week after initiation of TA treatment to the end of the test. For evaluation of disease state, blood and hepatic tissues were collected on the 10th and 20th weeks after the TA treatment. The collected hepatic tissues were subjected to hematoxylin-eosin (HE) and Sirius red staining, and the pathologic images were inputted to image analysis software (Image J) to evaluate hepatic fibrosis in terms of area ratio. The amount of hyaluronic acid in blood was measured using a hyaluronic acid ELISA kit (manufactured by CosmoBio Co., Ltd.). Furthermore, quantification of the amount of hydroxyproline in liver was performed by the Norman-Logan method.

All test results are expressed as the mean value±standard deviation (S.D.). Statistical analysis was performed using Dunnett's multiple comparison tests between the groups administered TA solution for 20 weeks, with a risk rate of 5% or less used as the significance level.

Figure 17:
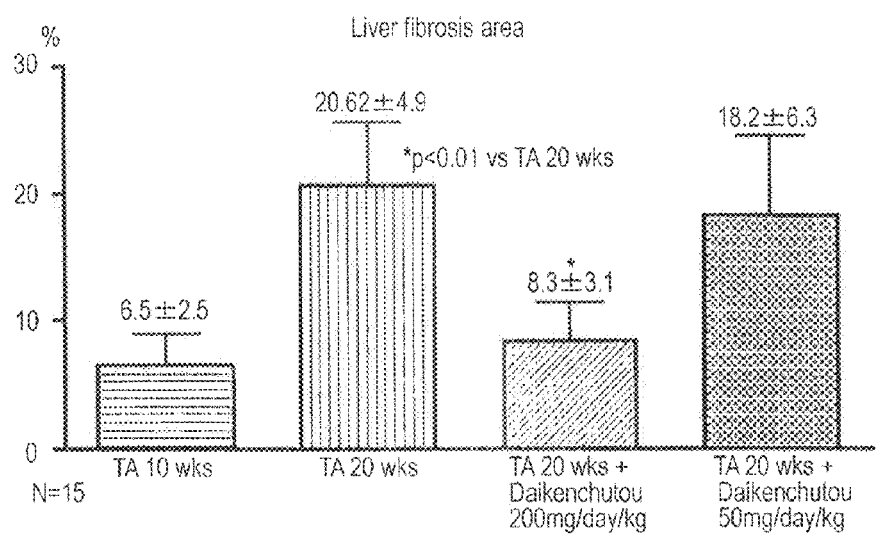
FIG. 17 is a diagram showing the results of measurement of hepatic fibrosis in Example 7.
Figure 18:
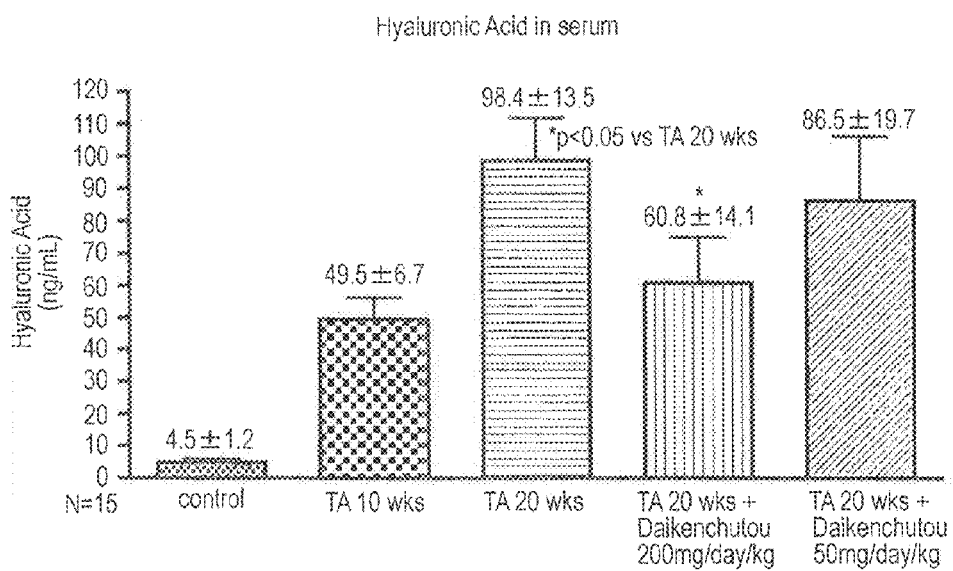
FIG. 18 is a diagram showing the results of quantification of the amount of hyaluronic acid in blood in Example 7.
Figure 19:
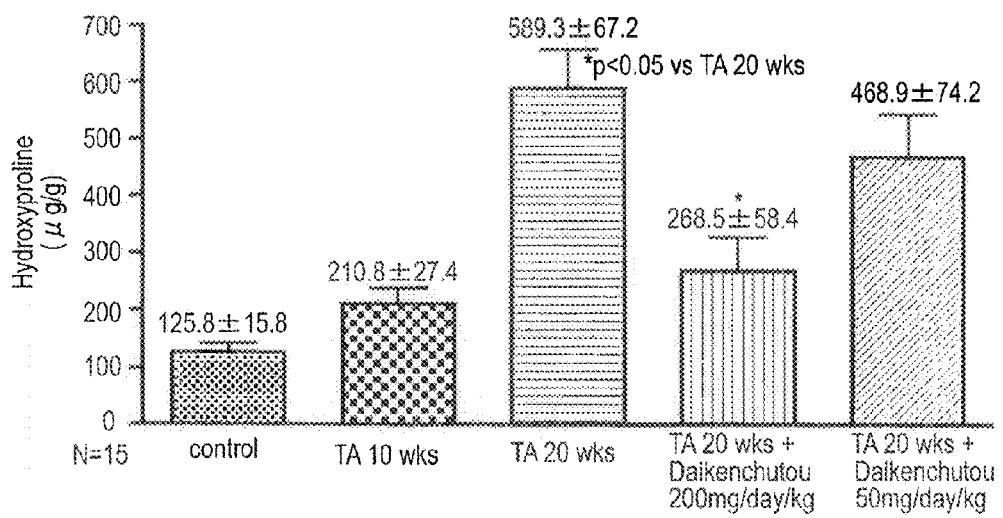
FIG. 19 is a diagram showing the results of quantification of the amount of hydroxyproline in liver in Example 7.

The results of evaluation of hepatic fibrosis are presented in FIG. 17, the results of measurement of the amount of hyaluronic acid in blood in FIG. 18, and the results of quantification of hydroxyproline in liver in FIG. 19.

In the hepatitis control group on the 10th and 20th week after TA treatment, levels of hyaluronic acid in blood and hydroxyproline in liver, which are markers of hepatic fibrosis, were each significantly increased compared to the untreated group, and increases in them were particularly obvious at the 20th week. In the hepatitis control group, at the 20th week after TA treatment, Sirius Red-positive pathological changes were clearly observed, and findings characteristic of hepatic cirrhosis were exhibited. On the other hand, in the group administered Daikenchutou from the 10th week after TA treatment and evaluated at the 20th week, increases in the levels of hyaluronic acid in blood and hydroxyproline in liver were significantly less than those in the control group, with clear manifestation of efficacy. These effects were confirmed by HE and Sirius Red staining. Daikenchutou thus inhibited progression of hepatic fibrosis and was clearly efficacious in a TA-induced model of hepatic cirrhosis.

Preparation Example 1

A 50 g portion of ginsenoside RID$_1$ and 50 g of hydroxysanshool were mixed with 270 g of lactose, 120 g of microcrystalline cellulose, and 10 g of magnesium stearate, and this mixture was tableted with a single punch tableting machine to produce tablets each weighing 250 mg and having a diameter of 9 mm.

Each of these tablets contains 25 mg each of ginsenoside Rb$_1$ and hydroxysanshool. The tablets are to be taken internally at a dose of 3 to 10 tablets a day in several divided portions according to symptoms.

Preparation Example 2

A 25 g portion of ginsenoside Rg$_1$ and 25 g of hydroxysanshool were mixed with 950 g of corn starch, and the mixture was kneaded by adding water. The resultant was granulated using a screen with a mesh size of 1 mm×1 mm and dried to obtain a granule preparation.

A 1 g portion of this granule preparation contains 25 mg each of ginsenoside Rg$_1$ and hydroxysanshool. The granule preparation is to be taken internally at a dose of 2 to 6 g a day in several divided portions according to symptoms.

Preparation Example 3

A 50 g portion of shogaol and 50 g of hydroxysanshool were mixed with 210 g of lactose, 120 g of starch, 50 g of talc, and 20 g of magnesium stearate, and the mixture was filled into hard capsules in amounts of 250 mg each to obtain a capsule preparation.

Each of these capsules contains 25 mg each of shogaol and hydroxysanshool. The capsule preparation is to be taken internally at a dose of 3 to 10 capsules a day in several divided portions according to symptoms.

Preparation Example 4

A 50 g portion of a ginseng extract and 50 g of a Japanese pepper extract were mixed with 270 g of lactose, 120 g of microcrystalline cellulose, and 10 g of magnesium stearate, and this mixture was tableted with a single punch tableting machine to produce tablets each weighing 250 mg and having a diameter of 9 mm.

Each of these tablets contains 25 mg each of the ginseng extract and the Japanese pepper extract. The tablets are to be taken internally at a dose of 3 to 10 tablets a day in several divided portions according to symptoms.

Preparation Example 5

A 25 g portion of a ginseng extract, 25 g of a Japanese pepper extract, and 25 g of a dried ginger rhizome extract were mixed with 925 g of corn starch, and the mixture was kneaded by adding water. The resultant was granulated using a screen with a mesh size of 1 mm×1 mm and dried to obtain a granule preparation.

A 1 g portion of the present granule preparation contains 25 mg each of the ginseng extract, Japanese pepper extract, and dried ginger rhizome extract. The granule preparation is to be taken internally at a dose of 2 to 6 g a day in several divided portions according to symptoms.

Preparation Example 6

Production of Daikenchutou Extract Granules

Crude drugs were cut out, and 3 kg of ginseng, 2 kg of Japanese pepper, and 5 kg of dried ginger rhizome were weighed and combined. Purified water was added thereto in an approximately 12-fold amount, and the temperature was raised to 95 to 100° C. while stirring. Extraction was then performed for about 60 minutes. After completion of the extraction, the extract was subjected to solid-liquid separation, and the separated liquid was concentrated under reduced pressure. Subsequently, sucrose fatty acid ester was added and mixed in an amount corresponding to 1.0% of the solid fraction, and the mixture was spray-dried to obtain 1.25 kg of dry extract. Then 10 kg of *Saccharum granorum* (powdered syrup), 3.7125 kg of lactose, and 0.0375 kg of magnesium stearate were added to 1.25 kg of the dried extract and mixed. This mixture was tableted with a tableting machine according to a conventional method, and the tablets were then subjected to pulverization, granulation, and sieving to obtain a satisfactory granule preparation.

A 15 g portion of the present granule preparation contains 1.25 g of a crude drug extract and 10 g of powdered syrup. The granule preparation is to be taken internally at a dose of 15 g a day in two to three divided portions according to symptoms.

INDUSTRIAL APPLICABILITY

The adrenomedullin production-enhancing agent of the invention effectively promotes the production of adrenomedullin, which has various physiological effects including increasing blood flow as well as anti-inflammatory effects. The sustainability of its effects and its safety are excellent. The adrenomedullin production-enhancing agent of the invention can thus be used in the treatment of various diseases, and is effective in the prevention and treatment of diseases including, for example, inflammatory bowel diseases such as Crohn's disease, myocardial disorders, pulmonary hypertension, bone disorders, myometrial contraction, urinary disorders, non-bacterial inflammatory disorders, and hepatitis.

The invention claimed is:

1. A method of increasing blood flow inside the intestinal tract, the method comprising administering to a subject in need thereof an effective amount of a composition comprising, as the only active ingredients, a hydroxysanshool and at least one of compound selected from the group consisting of ginsenoside $Rb_1$ and ginsenoside $Rg_1$ wherein the dosage ratio of the least one of compound selected from the group consisting of ginsenoside $Rb_1$ and ginsenoside $Rg_1$ to the hydroxysanshool is 10:3.

2. The method according to claim 1, wherein the composition comprises hydroxysanshool and ginsenoside $Rb_1$.

3. The method according to claim 1, wherein the composition comprises hydroxysanshool and ginsenoside $Rg_1$.

4. The method according to claim 1, wherein the composition comprises hydroxysanshool, ginsenoside $Rb_1$ and ginsenoside $Rg_1$.

5. The method according to claim 1, wherein the hydroxysanshool is at least one selected from the group consisting of hydroxy-α-sanshool, hydroxy-β-sanshool, and hydroxy-γ-sanshool.

6. The method of claim 1, wherein the hydroxysanshool and the at least one of compound selected from the group consisting of ginsenoside $Rb_1$ and ginsenoside $Rg_1$ are each administered in an amount ranging from 1 mg to 1 g per day.

7. A method of treating an inflammatory bowel disease, the method comprising administering to a subject in need thereof an effective amount of a composition comprising, as the only active ingredients, a hydroxysanshool and at least one of compound selected from the group consisting of ginsenoside $Rb_1$ and ginsenoside $Rg_1$ wherein the dosage ratio of the least one of compound selected from the group consisting of ginsenoside $Rb_1$ and ginsenoside $Rg_1$ to the hydroxysanshool is 10:3.

8. The method according to claim 7, wherein the inflammatory bowel disease is ulcerative colitis or Crohn's disease.

9. The method according to claim 7, wherein the composition comprises hydroxysanshool and ginsenoside $Rb_1$.

10. The method according to claim 7, wherein the composition comprises hydroxysanshool and ginsenoside $Rg_1$.

11. The method according to claim 7, wherein the composition comprises hydroxysanshool, ginsenoside $Rb_1$ and ginsenoside $Rg_1$.

12. The method according to claim 7, wherein the hydroxysanshool is at least one selected from the group consisting of hydroxy-α-sanshool, hydroxy-β-sanshool, and hydroxy-γ-sanshool.

13. The method of claim 7, wherein the hydroxysanshool and the at least one of compound selected from the group consisting of ginsenoside $Rb_1$ and ginsenoside $Rg_1$ are each administered in an amount ranging from 1 mg to 1 g per day.

* * * * *